United States Patent [19]
Keck et al.

[11] Patent Number: 5,240,848
[45] Date of Patent: Aug. 31, 1993

[54] DNA SEQUENCES ENCODING HUMAN VASCULAR PERMEABILITY FACTOR HAVING 189 AMINO ACIDS

[75] Inventors: Pamela J. Keck, St. Louis; Daniel T. Connolly, Manchester; Joseph Feder, University City, all of Mo.

[73] Assignee: Monsanto Company, St. Louis, Mo.

[21] Appl. No.: 377,037

[22] Filed: Jul. 10, 1989

Related U.S. Application Data

[63] Continuation-in-part of Ser. No. 274,061, Nov. 21, 1988.

[51] Int. Cl.$^5$ .................. C12N 15/00; C12N 15/12; C12N 15/19
[52] U.S. Cl. ........................ 435/240.2; 536/23.5; 536/23.51; 435/69.1; 435/320.1; 530/350; 530/399
[58] Field of Search ........... 536/27; 435/172.1, 172.3, 435/69.1, 69.6, 240.1, 240.2, 320.1, 948; 935/11, 23, 27, 32, 34, 70, 74

[56] References Cited

U.S. PATENT DOCUMENTS

| | | | |
|---|---|---|---|
| 4,456,550 | 6/1984 | Connolly et al. | 260/112 |
| 5,008,196 | 4/1991 | Connolly et al. | 435/240.2 |
| 5,038,003 | 7/1991 | Olander et al. | 435/70.1 |

OTHER PUBLICATIONS

Ferrara, N. et al., *J. Cell. Biochem.*, 47:211–218, 1991.
Winnicker, *From Genes to Clones*, pp. 239–381, 1987.
Connolly et al, "Human Vascular Permeability Factor", Journal of Biological Chemistry, vol. 264 (33), 20017–20024, 1989.
Sobel et al, "Physiochemical Characterization of a vascular permeability factor produced by Con-A-Stimulated human lymphocytes", J. Immun. vol. 119 (4), pp. 1230–1234, 1977.
Keck et al, "Vascular Permeability Factor, an endothelial cell nitrogen related to PDGF", Science, vol. 246, 1309–1312, 1989.
Suggs et al, "Use of synthetic oligonucleotides as hybridization probes: Isolation of cloned DNA sequences for human B2-microglobulin" PNAS, vol. 78(11) 6613–6617, 1981.
Senger et al., Science 219, 983–985 (1983).
Folkman and Klagsbrun, Science 235, 442–447 (1987).
Dvorak et al., J. Immunol. 122(1) 166–174 (1979).
Dvorak, N. Engl. J. Med. 315, 1650–1659 (1986).
Kadish et al., Tissue & Cell 11, 99 (1979).
Dvorak et al., J. Natl. Cancer Inst. 62, 1459–1472 (1979).
Lobb et al., Int. J. Cancer 36, 473–478 (1985).
Senger et al., Cancer Res. 46, 5629–5632 (1986).
Beck and Habicht, J. Leukocyte Biol. 42, 568 Absts., Dec. 1987, No. 82.

*Primary Examiner*—Robert J. Hill, Jr.
*Assistant Examiner*—Marianne Porta Allen
*Attorney, Agent, or Firm*—Scott J. Meyer

[57] ABSTRACT

A cDNA having a base sequence for human vascular permeability factor has been cloned and characterized and the amino acid sequence of the human vascular permeability factor protein has been determined.

8 Claims, 5 Drawing Sheets

DNA SEQUENCES ENCODING HUMAN VASCULAR PERMEABILITY FACTOR HAVING 189 AMINO ACIDS

CROSS-REFERENCE TO RELATED APPLICATION

This is a continuation-in-part of application Ser. No. 07/274,061, filed Nov. 21, 1988.

BACKGROUND OF THE INVENTION

This invention relates to a novel human vascular permeability factor and to a cDNA clone representing the full size human vascular permeability factor protein.

Vascular permeability factors (VPFs) are proteins originally obtained from a variety of tumors which cause a rapid and reversible increase in blood vessel permeability when nanogram amounts are injected under the skin of a warm blooded mammal. VPF activity has been found in tumor ascites fluid from guinea pigs, hamsters and mice and is secreted by these tumors and a variety of tumor cell lines in vitro according to Senger et al., Science 219, 983-985 (1983).

In U.S. Pat. No. 4,456,550, a purified VPF is described which has the following characteristics:
(a) in an aqueous solution (0.01 M Na$_3$PO$_4$, pH 7) whose concentration of NaCl is varied linearly, VPF is eluted from a heparin-Sepharose chromatography column in a peak centered at 0.4 NaCl;
(b) in an aqueous solution of Na$_3$PO$_4$, pH 7.0, whose concentration is varied linearly, VPF is eluted from a hydroxylapatite column in a peak centered at 0.25 M Na$_3$PO$_4$; and
(c) when subjected to SDS gel electrophoresis in a polyacrylamide slab gel (0.375 M tris-HCl, pH 8.8, 0.1% SDS) at 35 milliamps and 4° C., VPF is localized to a region corresponding to a molecular weight between 34,000 and 45,000 daltons.

VPF of the foregoing characteristics was thus purified about 1800 fold from serum-free conditioned medium of guinea pig tumor cell culture or 10,000 fold from ascites fluid by a series of steps consisting of:
(a) affinity chromatography with a column of heparin-Sepharose;
(b) chromatography with a column of hydroxylapaptite; and
(c) sodium dodecylsulfate/polyacrylamide gel electrophoresis.

According to said patent, as little as 200 ng (5×10$^{-12}$ moles) of this purified VPF increased the vascular permeability equivalent to 1.25 μg (4×10$^{-9}$ moles) of histamine. Histamine is a standard permeability mediator described by Miles and Miles, J. Physiol. 118, 228-257 (1952). The VPF is said to have therapeutic value insofar as it enables blood nutrients to reach tissue with increased need for nutrients, as in wound healing.

According to Folkman and Klagsbrun, Science 235, 442-447 (1987), VPF causes leakage of proteins, including fibrinogen, from blood vessels, thereby initiating the formation of a fibrin gel which, in turn, may play a role in angiogenesis. See also Dvorak et al., J. Immunol. 122(1), 166-174 (1979); Dvorak, N. Engl. J. Med. 315, 1650-1659 (1986); Kadish et al., Tissue & Cell 11, 99 (1979); and Dvorak et al., J. Natl. Cancer Inst. 62, 1459-1472 (1979).

In copending application Ser. No. 07/87,739, filed Aug. 31, 1987, and assigned to a common assignee, a method of stimulating endothelial cell growth is provided which comprises subjecting said cells to a growth stimulating amount of a highly purified VPF. The highly purified VPF derived from guinea pig tumor cells has the following characteristics:
(a) it has a M$_r$ about 34,000-40,000 as determined by sodium dodecylsulfate polyacrylamide gel electrophoresis (SDS/PAGE);
(b) it is a disulfide-linked protein dimer;
(c) it has a N-terminal amino acid sequence as follows:

```
1           5              10             15
AlaProMetAlaGluGlyGluGlnLysProArgGluValValLys 16          20             25             30
PheMetAspValTyrLysArgSerTyrCysArgProIleGluMet 31          35
LeuValAspIlePheGln; and
```

(d) it exhibits substantial mitogenic activity to endothelial cells in culture.

The foregoing highly purified guinea pig VPF, also referred to as gVPF, was isolated from serum-free conditioned culture medium of guinea pig tumor cells in a series of steps comprising:
(a) affinity chromatography of said conditioned culture medium with a column of heparin-Sepharose CL-6B;
(b) cation exchange chromatography of the VPF active fractions from said affinity chromatography with a TSK SP-5-PW column;
(c) high performance liquid chromatography (HPLC) of the VPF active fractions from said cation exchange chromatography with a Vydac C$_4$ reversed phase HPLC column; and
(d) HPLC of the VPF active fractions from said C$_4$ HPLC with a Vydac C$_{18}$ reversed phase HPLC column.

In copending application Ser. No. 780, filed Sep. 2, 1988, and assigned to a common assignee, a method of producing antibodies against gVPF is provided in which certain peptide fragments of gVPF are used as immunogens.

Lobb et al., Int. J. Cancer 36, 473-478 (1985), describe a partially purified VPF from a human adenocarcinoma cell line HT-29 having a molecular weight of 45,000. This VPF, however, does not bind to immobilized heparin as does the VPF derived from guinea pig tumor cell material by Senger and Dvorak.

Senger et al., Cancer Res. 46, 5629-5632 (1986), describe the production of VPF from a variety of human tumor cell lines, namely human osteogenic sarcoma, bladder sarcoma, cervical carcinoma and fibrosarcoma cell lines. However, none of these human cell lines were found to be as active as the guinea pig cell line 10 for the producton of VPF.

BRIEF DESCRIPTION OF THE INVENTION

In accordance with the present invention, a cDNA clone representing the full size human vascular permeability factor (hVPF) has been developed. This clone, VPF-4, contains about 3550 base pairs (bp) with an apparent 5'-noncoding region of about 1300 bp, an open reading frame of 645 bp, a stop codon and a 3'-noncoding region of about 1600 bp.

The cDNA sequence encodes a hVPF protein of 215 amino acids. This protein sequence includes a putative signal peptide of 26 amino acids beginning with a methionine residue positioned 26 amino acids upstream to the NH₂-terminus, followed by the 189 amino acid mature protein.

The hVPF contains a potential N-glycosylation site at Asn 75 and 16 cysteine residues. A zinc-finger like region is noted at amino acids 57–90.

Within the hVPF sequence, four amino acid segments correspond to the previously sequenced segments from the U-937 secreted protein described in copending application Ser. No. 07/274,061, filed Nov. 21, 1988. These include the first 10 amino acids of the NHz-terminus, namely $$\overset{1}{A} P M A E G G G Q \overset{10}{N},$$

and three internal peptide fragments which correspond to amino acid residues:

(a) $\overset{17}{F} M D V Y Q \overset{23}{R}$, (b) $\overset{33}{V} D I F Q E Y P D E I E \overset{45}{Y}$, and (c) $\overset{46}{I} F K P S C V P L M \overset{56}{R}$.

The cDNA sequence and corresponding predicted amino acid sequence of the hVPF is shown in the following 1195 bp sequence which includes portions of the 5'- and 3'- noncoding regions. Nucleotides are numbered in the lefthand column, beginning with No. 1. Amino acids are numbered from above. The predicted amino acid sequences from the cDNA clone for amino acid positions 1-18, 17-23, 33-45 and 46-56 exactly match amino acid sequences determined by amino acid sequencing of the N-terminus and of three different tryptic peptides. These sequences are underlined. The single N-glycosylation site at Asn-75 is boxed. The stop codon is designated with three asterisks.

| | | | | | |
|---|---|---|---|---|---|
| 1 | GCGCAGACAG | TGCTCCAGCG | CGCGCGCTCC | CCAGCCCTGC | CCGGCCTCGG |
| 51 | GCCGGGAGGA | AGAGTAGCTC | GCCGAGGCGC | CGAGGAGAGC | GGGCCGCCCC |
| 101 | ACAGCCCGAG | CCGGAGAGGG | ACGCGAGCCG | CGCGCCCCGG | TCGGGCCTCC |

| | | -26 Met ATG | Asn AAC | Phe TTT | Leu CTG | Leu CTG | Ser TCT | -20 Trp TGG | Val GTG | His CAT | Trp TGG | Ser AGC | Leu CTT |
|---|---|---|---|---|---|---|---|---|---|---|---|---|---|
| 151 | GAAACC | | | | | | | | | | | | |

| | Ala GCC | Leu TTG | Leu CTG | Leu CTC | -10 Tyr TAC | Leu CTC | His CAC | His CAT | Ala GCC | Lys AAG | Trp TGG | Ser TCC | Gln CAG | Ala GCT |
|---|---|---|---|---|---|---|---|---|---|---|---|---|---|---|
| 193 | | | | | | | | | | | | | | |

| | +1 Ala GCA | Pro CCC | Met ATG | Ala GCA | Glu GAA | Gly GGA | Gly GGA | Gly GGG | Gln CAG | 10 Asn AAT | His CAT | His CAC | Glu GAA | Val GTG |
|---|---|---|---|---|---|---|---|---|---|---|---|---|---|---|
| 235 | | | | | | | | | | | | | | |

| | Val GTG | Lys AAG | Phe TTC | Met ATG | Asp GAT | 20 Val GTC | Tyr TAT | Gln CAG | Arg CGC | Ser AGC | Tyr TAC | Cys TGC | His CAT | Pro CCA |
|---|---|---|---|---|---|---|---|---|---|---|---|---|---|---|
| 277 | | | | | | | | | | | | | | |

| | Ile ATC | 30 Glu GAG | Thr ACC | Leu CTG | Val GTG | Asp GAC | Ile ATC | Phe TTC | Gln CAG | Glu GAG | Tyr TAC | 40 Pro CCT | Asp GAT | Glu GAG |
|---|---|---|---|---|---|---|---|---|---|---|---|---|---|---|
| 319 | | | | | | | | | | | | | | |

| | Ile ATC | Glu GAG | Tyr TAC | Ile ATC | Phe TTC | Lys AAG | Pro CCA | 50 Ser TCC | Cys TGT | Val GTG | Pro CCC | Leu CTG | Met ATG | Arg CGA |
|---|---|---|---|---|---|---|---|---|---|---|---|---|---|---|
| 361 | | | | | | | | | | | | | | |

| | Cys TGC | Gly GGG | Gly GGC | 60 Cys TGC | Cys TGC | Asn AAT | Asp GAC | Glu GAG | Gly GGC | Leu CTG | Glu GAG | Cys TGT | Val GTG | 70 Pro CCC |
|---|---|---|---|---|---|---|---|---|---|---|---|---|---|---|
| 403 | | | | | | | | | | | | | | |

| | Thr ACT | Glu GAG | Glu GAG | Ser TCC | Asn AAC | Ile ATC | Thr ACC | Met ATG | Gln CAG | 80 Ile ATT | Met ATG | Arg CGG | Ile ATC | Lys AAA |
|---|---|---|---|---|---|---|---|---|---|---|---|---|---|---|
| 445 | | | | | | | | | | | | | | |

| | Pro CCT | His CAC | Gln CAA | Gly GGC | Gln CAG | 90 His CAC | Ile ATA | Gly GGA | Glu GAG | Met ATG | Ser AGC | Phe TTC | Leu CTA | Gln CAG |
|---|---|---|---|---|---|---|---|---|---|---|---|---|---|---|
| 487 | | | | | | | | | | | | | | |

| | His CAC | 100 Asn AAC | Lys AAA | Cys TGT | Glu GAA | Cys TGC | Arg AGA | Pro CCA | Lys AAG | Lys AAA | Asp GAT | 110 Arg AGA | Ala GCA | Arg AGA |
|---|---|---|---|---|---|---|---|---|---|---|---|---|---|---|
| 529 | | | | | | | | | | | | | | |

| | Gln CAA | Glu GAA | Lys AAA | Lys AAA | Ser TCA | Val GTT | Arg CGA | 120 Gly GGA | Lys AAG | Gly GGA | Lys AAG | Gly GGG | Gln CAA | Lys AAA |
|---|---|---|---|---|---|---|---|---|---|---|---|---|---|---|
| 571 | | | | | | | | | | | | | | |

| | Arg CGA | Lys AAG | Arg CGC | 130 Lys AAG | Lys AAA | Ser TCC | Arg CGG | Tyr TAT | Lys AAG | Ser TCC | Trp TGG | Ser AGC | Val GTT | 140 Pro CCC |
|---|---|---|---|---|---|---|---|---|---|---|---|---|---|---|
| 613 | | | | | | | | | | | | | | |

-continued

| | | | | | | | | | 150 | | | | |
|---|---|---|---|---|---|---|---|---|---|---|---|---|---|
| | Cys | Gly | Pro | Cys | Ser | Glu | Arg | Arg | Lys | His | Leu | Phe | Val | Gln |
| 655 | TGT | GGG | CCT | TGC | TCA | GAG | CGG | AGA | AAG | CAT | TTG | TTT | GTA | CAA |
| | | | | | | 160 | | | | | | | | |
| | Asp | Pro | Gln | Thr | Cys | Lys | Cys | Ser | Cys | Lys | Asn | Thr | Asp | Ser |
| 697 | GAT | CCG | CAG | ACG | TGT | AAA | TGT | TCC | TGC | AAA | AAC | ACA | GAC | TCG |
| | | 170 | | | | | | | | | | 180 | | |
| | Arg | Cys | Lys | Ala | Arg | Gln | Leu | Glu | Leu | Asn | Glu | Arg | Thr | Cys |
| 739 | CGT | TGC | AAG | GCG | AGG | CAG | CTT | GAG | TTA | AAC | GAA | CGT | ACT | TGC |
| | Arg | Cys | Asp | Lys | Pro | Arg | Arg | *** | | | | | | |
| 781 | AGA | TGT | GAC | AAG | CCG | AGG | CGG | TGA | GCCGGGCAGG | | AGGAAGGAGC | | | |
| 825 | CTCCCTCAGG | | GTTTCGGGAA | | CCAGATCTCT | | CACCAGGAAA | | GACTGATACA | | | | | |
| 875 | GAACGATCGA | | TACAGAAACC | | ACGCTGCCGC | | CACCACACCA | | TCACCATCGA | | | | | |
| 925 | CAGAACAGTC | | CTTAATCCAG | | AAACCTGAAA | | TGAAGGAAGA | | GGAGACTCTG | | | | | |
| 975 | CGCAGAGCAC | | TTTGGGTCCG | | GAGGGCGAGA | | CTCCGGCGGA | | AGCATTCCCG | | | | | |
| 1025 | GGCGGGTGAC | | CCAGCACGGT | | CCCTCTTGGA | | ATTGGATTCG | | CCATTTTATT | | | | | |
| 1075 | TTTCTTGCTG | | CTAAATCACC | | GAGCCCGGAA | | GATTAGAGAG | | TTTTATTTCT | | | | | |
| 1125 | GGGATTCCTG | | TAGACACACC | | CACCCACATA | | CATACATTTA | | TATATATATA | | | | | |
| 1175 | TATTATATAT | | ATATAAATTA | | A | | | | | | | | | |

The gene coding for the hVPF of this invention can be cloned into and expressed in prokaryotic and eukaryotic hosts. For example, active hVPF protein can be expressed in a prokaryotic host such as E. coli and a eukaryotic host such as C-127 mouse cells or Chinese hamster ovary (CHO) cells by operably inserting the hVPF coding sequence in replicable expression vectors or plasmids. For example, it can be inserted into a suitable plasmid such as pML for production in E. coli and the bovine papilloma virus (BPV) vector for production in mouse cells or a shuttle vector which can replicate in both prokaryotic and eukaryotic cells. In a preferred embodiment, the gene coding for the hVPF was cloned into and expressed from C-127 mouse cells. The excreted protein was determined by the assay of Miles and Miles, supra, (hereinafter also referred to as the Miles assay).

The original source material for the production of hVPF is the human histiocytic lymphoma cell line U-937 as described in said copending application Ser. No. 07/274,061. This cell line was originally established from cells from the pleural effusion of a patient with diffuse histiocytic lymphoma as reported by Sundstrom and Nilsson, Int. J. Cancer 17, 565-577 (1976). These cells are widely distributed as evidenced by publications and are also readily available to the public in an unrestricted culture deposit from the American Type Culture Collection, Rockville, Maryland, under accession number ATCC CRL 1593. Further background on these cells can be had by reference to J. Exp. Med. 143, 1528-1533 (1976); Nature 279, 328-331 (1979); and J. Immunol. 125, 463-465 (1980).

A recent report on the use of U-937 cells to produce VPF-like activity was made by Beck and Habicht, J. Leukocyte Biol. 42, 568 Absts., Dec. 1987. However, the activity was not purified and chemical characterization or identity was not disclosed.

The human VPF produced by U-937 cells was originally identified by its inhibition and binding by rabbit polyclonal antibodies to guinea pig VPF as described in said copending application Ser. No. 07/274,061. A rabbit polyclonal antiserum to guinea pig VPF inhibited the permeability activity produced by U-937 cells as determined by the of Miles assay. This U-937 generated VPF activity was about 70% to 80% removed by binding to immunoadsorbents produced with protein A-Sepharose ® which had been reacted with the rabbit polyclonal antiserum to guinea pig VPF.

A suitable process for the production of human VPF is described in said copending application Ser. No. 07/274,061. The process comprises growing cells derived from the human histiocytic lymphoma cell line U-937 in serum-free nutrient culture medium at about 35° to 38° C. for a sufficient time to elaborate VPF and isolating the resulting VPF from the spent cells or the cell culture conditioned medium.

A preferred method of isolating the human VPF from the cell culture conditioned medium of the U-937 cells described in said co-pending application comprises the following steps:
(a) cation exchange chromatography of said conditioned cell culture medium, for example with a column of CM-cellulose, CM-Sephadex ®, Amberlite° IR-120H or S-Sepharose Fast Flow cation exchanger;
(b) metal affinity chromatography of the VPF active fractions from said cation exchange chromatography, for example with a $Cu^{2+}$, $Zn^{2+}$ or $Ni^{2+}$/iminodiacetic acid(IDA)/Sepharose column; and
(c) reverse phase HPLC of the active VPF fractions from said method affinity chromatography, for example with a $C_4$ or $C_{18}$ reverse phase HPLC column.

The thus purified human VPF was found to be a protein of $M_4$ 34,000-42,000. When subjected to N-terminal amino-acid sequence analysis, it was found to have a distinct and novel structure whereby it differed from gVPF in four of the first ten amino acid positions.

The purified hVPF was active in promoting vessel leakage at a dose of 22 ng ($5.5 \times 10^{-13}$ Moles) upon intradermal injection into guinea pigs. This highly purified hVPF thus is 9 times more potent than 15 the gVPF described in U.S. Pat. No. 4,456,550. Another advantage of hVPF of this invention is its human origin which is indicative of potential use as a human therapeutic compared to other agents of lesser purity or derived from guinea pig or other animals such as would cause immunological reactions.

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments of the invention taken in conjunction with the accompanying drawings in which:

FIGS. 2A-2D are graphical representation which show the elution patterns in the stepwise purification of the hVPF in four panels 2A, 2B, 2C and 2D in the embodiment of FIG. 1 as follows:

2A) Cation Exchange Chromatography of hVPF. Serum-free conditioned medium from U-937 cells (6 L of 6-fold concentrate) was adjusted to pH 7.0 and loaded at a flow rate of 60 ml/hr onto an S-Sepharose column (5×45 cm) equilibrated in 0.01 M sodium phosphate, pH 7.0. A linear gradient from 0.2 M to 0.8 M NaCl in the same buffer was used to elute hVPF.

2B.) Metal Affinity Chromatography of hVPF. The active eluate from the cation exchange column was concentrated to 20 ml by ultrafiltration and loaded onto a Sepharose (Fast Flow)/IDA/$Cu^{+2}$ column equilibrated in 0.01 M sodium phosphate, pH 7.0, 2 M sodium chloride, 0.5 M imidazole. hVPF was eluted with a linear gradient of imidazole as shown.

2C.) RP-HPLC of hVPF. The active eluate from the metal affinity column was loaded onto a $C_{18}$ a RP-HPLC column equilibrated with 0.05% trifluoroacetic acid (TFA) in water and eluted at 1 ml/min with a gradient of acetonitrile as shown.

2D.) Sodium Dodecylsulfate-Polyacrylamide Gel Electrophoresis (SDS-PAGE) of RP-HPLC Fractions. Aliquots were removed from fractions around the activity peak and analyzed by electrophoresis without reducing agent. Standards were first reduced with $\beta$-mercaptoethanol.

FIGS. 3A-3B show the ELISA of hVPF and gVPF. Rabbit anti-gVPF IgG was used to coat the polystyrene wells of microtiter plates. Various amounts of either hVPF (lower panel) or gVPF (upper panel) were allowed to bind overnight, and the amount of bound antigen detected with biotin-anti-gVPF IgG followed by HRP-avidin. Wells were developed with HRP substrate, the absorbance was read at 490 nm. Wells containing readings that were off scale were diluted and re-read in the linear range of the Bio-Tek microplate reader; the absorbances given are corrected for dilution. Different x-axis scales were used for hVPF and gVPF. Early and late bleed refers to both primary and secondary biotin-conjugated IgGs prepared from sera collected at the fourth bleed (after 3 immunizations) and at the eleventh bleed (after 5 immunizations), respectively.

Figure 4:
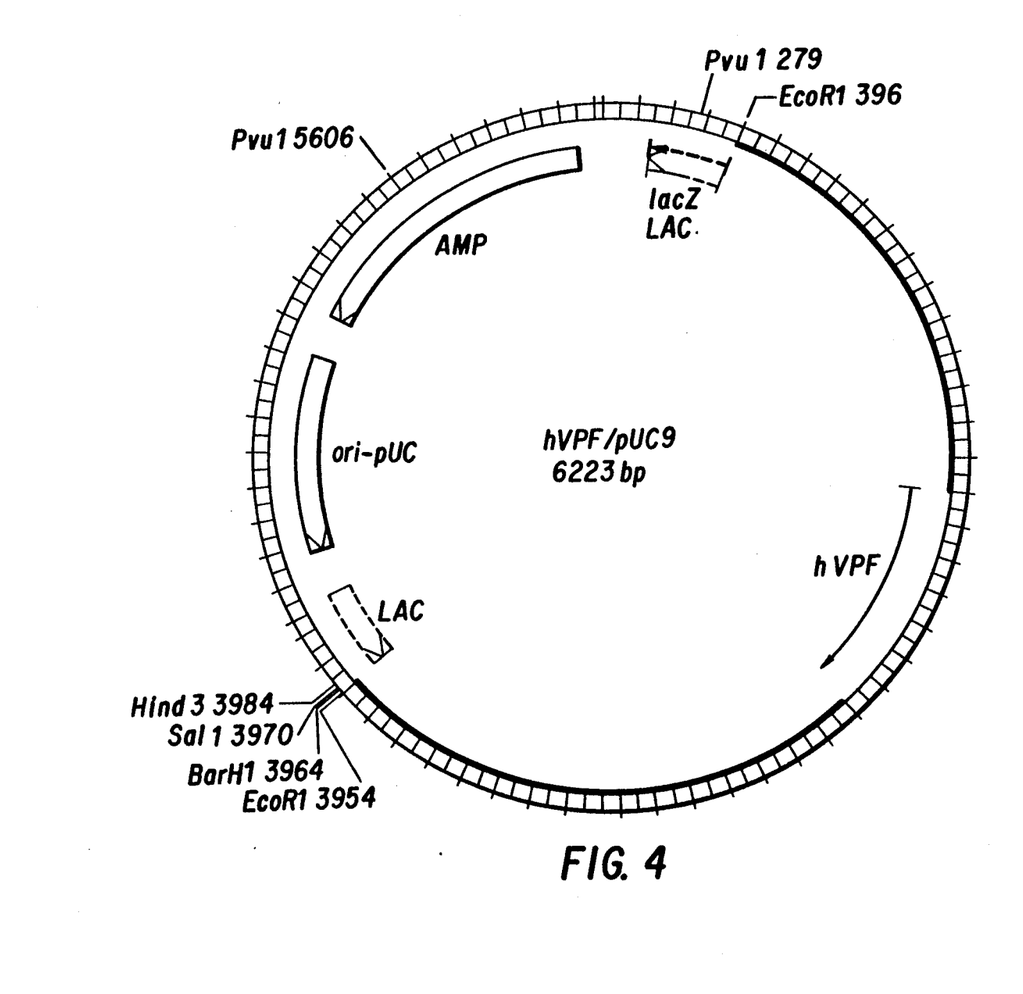

FIG. 4 shows the structure of plasmid hVPF/pUC9 of about 6200 bp. This plasmid, also designated pMON3044, contains the hVPF cDNA. The heavy arrow represents the location of the coding region for hVPF within the 3.5 kb cDNA.

Plasmid pUC9 is a commercially available versatile vector that contains a multiple cloning site and a gene that confers ampicillin (AMP) resistance. The plasmid produces the α-peptide of β-galactosidase which complements the lac deletion mutation in *E. coli* strains such as DH5a, JM83 and TB1.

Standard biochemical nomenclature is used herein in which the nucleotide bases of DNA or oligonucleotides are designated as adenine (A); thymine (T); guanine (C); and cytosine (C). N connotes any of these nucleotides. As is conventional for convenience in the structural representation of a DNA nucleotide sequence, only one strand is usually sown in which A on one strand connotes T on its complement and G connotes C. All sequences are written 5' to 3'. Amino acids are shown either by three letter or one letter abbreviations as follows:

| Abbreviated Designation | | Amino Acid |
|---|---|---|
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Commonly available restriction endonucleases shown in Example 4 and FIG. 4 have the following restriction sequences and (indicated by arrows) cleavage patterns.

The U-937 cells can be cultured in well-known cell culture media such as basal medium Eagle's (BME), Dulbecco's modified Eagle medium (DMEM), medium 199, RPMI 1640 medium, and the like cell culture media such as described in detail by H. J. Morton, *In Vitro* 6, 89–108 (1970). These conventional culture media contain known amino acids, mineral salts, vitamins, hormones and carbohydrates. They are also frequently fortified with mammalian sera such as fetal bovine serum (FBS). Other components which can be used in the media are bovine serum albumin (BSA), growth factors such as transferrin and insulin, protein hydrolysates such as lactalbumin hydrolysate, tryptone, tryptose and peptone, as well as lipids, surfactants and the like materials. The U-937 cells preferably are cultured in serum-free media for the production of hVPF.

Methods for the large scale growth of mammalian cells are well-known and these methods can be used for the culture of the U-937 cells defined herein. Such methods are described, for example, by Tolbert et al., *Biotech. Bioeng.* XXIV, 1671-1679 (1982); Tolbert and Feder, *Ann. Rept. Ferm. Proc.* Vol. 6, Ch. 3, pp. 35-74 (1983); Harakas, Ibid. Vol. 7, Ch. 7, pp. 159-211 (1984); and references cited in said publications. U.S. Pat. Nos. 4,166,768; 4,289,854; and 4,537,860 disclose particularly useful methods and apparatus for the large scale growth and maintenance of cells for the production of proteinaceous materials. The disclosures in said patents are incorporated herein by reference. The methods and apparatus disclosed therein can be used for the culture of the U-937 cells defined herein.

The cells also can be cultured on a large scale basis in nutrient medium at 37° C. in agitated suspension culture as described in U.S. Pat. No. 4,289,854 and, after a suitable growth period, can be maintained in the static maintenance reactor described in U.S. Pat. No. 4,537,860 in which the medium is supplemented with 0.5% lactalbumin hydrolysate.

Although purification of the hVPF from the spent culture media can employ various known procedures for the separation of proteins such as, for example, salt and solvent fractionation, adsorption with colloidal materials, gel filtration, ion exchange chromatography, affinity chromatography, immuno-affinity chromatography, electrophoresis and high performance liquid chromatography (HPLC), the above described three-step chromatographic method is preferred. Suitable metal affinity chromatography procedures are illustrated by Sulkowski, *Trends Biotech.* 3, 1-7 (1985).

In a preferred process the U-937 cells are subcloned or passaged through nude mice to improve the yield of hVPF. Such treatment of the cells has provided for the production of hVPF in quantities of up to 200 to 800 ng/ml of the conditioned medium. This is equivalent to or greater than the gVPF levels reported for the guinea pig cell Line 10.

The U-937 cells have been passaged through nude mice by injection of $1 \times 10^7$ cells into the mouse peritoneum. Nude mice are an immunodeficient species in which human cells can grow and not be rejected. After about 3 to 4 weeks, the mice were sacrificed and soft tumors were removed from their abdomens. The tumors were mechanically dissociated into cells and these U-937 cells were again put into culture.

The following examples will further illustrate the invention although it will be appreciated that the invention is not limited to these specific examples or the details described therein.

EXAMPLE 1

Materials and Methods

Growth of U-937 Cells

U-937 cells originally obtained from the American Type Culture Collection (ATCC) were subcloned in soft agar and selected for fast growth. One of these clones was selected for scale-up, but other clones, and even uncloned ATCC cells, also produced hVPF. The serum-free medium used contained the following components: RPMI 1640, DME (high glucose), Ham's F12 in a 1:1:1 ratio; HEPES (25 mM, pH 7.10-7.15); glutathione (1 mM); ethanolamine (20 µM); selenium (30 nM); $NaHCO_3$ (2 mM); $CuSO_4$ (5 nM); $NH_4VOs$ (5 nM); $ZnSO_4$ (0.5 µM); $MnSO_4$ (0.5 nM); $FeSO_4$ (4 µM); bovine serum albumin, Miles "Pentex" (100 µg/ml); iron rich transferrin, Miles (5 µg/ml); bovine insulin (10 µg/ml); ExCyte, Miles-lipid fraction (0.1% v/v); F-68 Pluracol ® (0.05% w/v). The volume was adjusted to yield an osmolarity of 280 mOsm. The doubling time was about 50-60 hours in this medium, whereas it was only 35-40 hours in medium containing 2% fetal bovine serum (FBS).

Cells were scaled-up in the serum-free medium from T-flasks into roller bottles and then into small spinners. A 12 L spinner was then used to innoculate a 14 L perfusion chemostat which was perfused at a rate of approximately 3 ml medium/hour/ml of total packed cells. The culture was subsequently transferred to a 100 L perfusion chemostat, which was perfused under limiting nutrient conditions (1.5-2.0 ml medium/hour/ml packed cells, or 0.1-0.15 ml/day/million cells). Cells were recycled to the reactor using an AG Technology hollow fiber-cartridge (model CFP-4-E-6, 0.4 micron). Cell density ranged from $1.0 \times 10^6$ to $4.6 \times 10^6$ viable cells/ml, 3.0 to 23 ml/L of packed cells, and viability ranged from 64% to 84%. The production run in the 100 L reactor lasted 24 days, during which time a total of 1000 L of serum free conditioned medium was produced.

The permeate from the perfusion reactor was collected and stored at 4° C. Concentration was performed in 200-300 L lots on an Amicon DC-30 ultrafiltration apparatus with three low protein binding 10 kDa cutoff spiral cartridges (Amicon SIOY10) operated in parallel. A concentration of about 6 fold was achieved, including a phosphate buffered saline (PBS) wash of the cartridges and equipment that was pooled with the concentrate. The concentrate was stored at $-20°$ C.

Vascular Permeability Assay.

A Miles-type permeability assay (Miles and Miles, supra) was used to detect hVPF. Hairless guinea pigs (IAF/HA-HO, Charles River, Wilmington MA) were anesthetized by inhalation of methoxyflurane (Metofane ®, Pitman-Moore, Inc.). A 1 ml volume of 0.5% (w/v) Evan's blue dye (Sigma Chemical Co.) prepared in sterile saline for injection (Abbott Laboratories) was injected intracardially into the circulation. Samples for hVPF determination were prepared at appropriate dilutions in saline or phosphate buffered saline, and 200 µl volumes injected intradermally into sites on the back of the guinea pig. The presence of hVPF was indicated by an intense blue spot at the site of the injection where dye (bound to serum protein) had leaked from the circulation into the tissues.

Cation Exchange Chromatography.

Six liters of six-fold concentrated conditioned medium was adjusted to pH 7.0 with acetic acid and passed through a column (5 cm×44 cm) of S Sepharose ® Fast Flow (Pharmacia) cation exchange gel equilibrated with 0.01 M sodium phosphate, pH 7.0. At 4° C. a significant portion of the permeability enhancing activity passed through the column, but at ambient temperature (25° C.) 50 to 70% of the activity became bound to the column. This step was therefore regularly performed at room temperature. Sodium azide (0.01% w/v) was added to all buffers. Flow rates for loading and elution were 10 ml per minute. After loading, the column was washed with 900 ml of 0.01 M sodium phosphate, pH 7.0, and then eluted with a 2.3 L linear gradient containing from 0.2 M to 0.8 M sodium chloride in the same buffer. Between runs, the column was washed with 0.1 M sodium hydroxide before re-equilibrating with 0.01 M sodium phosphate, pH 7.0.

Metal Affinity Chromatography

Metal affinity chromatography was performed using a copper-iminodiacetic acid complex covalently linked to agarose via a spacer arm. The gel was synthesized in two steps by first adding an epoxide-containing spacer arm to the agarose, and then reacting the activated gel with iminodiacetic acid.

Highly cross-linked agarose (Sepharose Fast Flow, Pharmacia) was repeatedly washed with distilled water to remove all buffers and preservatives and then dried by suction. About 100 g (100 ml) of this damp gel was suspended in 60 ml distilled water, and then 40 ml freshly prepared 2.5 M NaOH solution was added to the gently stirring agarose suspension. Then 100 ml diethyleneglycol diglycidyl ether, prepared as described by Gu et al., *Synthesis*, 649-651 (1983), was added, and the mixture was gently stirred at 30° C. for 16 hours. The activated gel was repeatedly washed with distilled water to remove the excess epoxide and base. The washed, suction-dried gel contained 70 micromoles active epoxide groups per mL gel. The activated gel was stored in distilled water at 4° C. and generally used within 24 hours of preparation.

About 100 ml (100 g) of the activated Sepharose Fast Flow was washed with distilled water, dried by suction, and suspended in 100 ml of 1.0 M $Na_2NH(CH_2CO_2)-H_2O$ solution, which was adjusted to pH =11.0. This mixture was gently stirred at 65° C. for 24 hours and then repeatedly washed with distilled water to remove excess ligand. The functionalized gel was stored in ethanol/water (25/75 v/v) at 4° C. until ready for use. Titration with thiosulfate showed the absence of epoxide groups, so capping with ethanolamine was deemed unnecessary. To determine the metal binding capacity of the gel, 10 ml of suction-dried gel was saturated with excess 50 mM $Cu(ClO_4)_2$ and then carefully washed with distilled water. Finally, the bound copper was removed with an excess of 50 mM NazHzEDTA. Using standardized copper-EDTA solutions for comparison, the copper content was photometrically determined to be 43 micromoles Cu per milliliter of damp, suction-dried gel.

Chromatography was performed in a glass column (1.0×13 cm.) containing 10 ml of gel. The gel was charged with a 50 mM solution of $Cu(ClO_4)_2$, pH=4.5, and then saturated with a buffered imidazole solution (20 mM imidazole +2 M NaCl +50 mM $NaH_2PO_4$, pH 7.0). After thoroughly washing with 1.0 M NaCl, the column was then equilibrated with the starting buffer (50 mM $NaH_2PO_4$, pH 7.0, 2 M NaCl, 0.5 mM imidazole). The fractions from the cation exchange step containing permeability enhancing activity were pooled and concentrated from a volume of about 700 ml to 20 ml using an Amicon YM5 membrane. Upon concentration, a protein precipitate usually formed that could be removed by filtration. The sample was applied to the column at ambient temperature (25° C) and eluted at a flow rate of 0.5 ml/min over 500 minutes with a linear gradient of imidazole (0.5 mM to 60 mM) in 50 mM $NaH_2PO_4$, pH 7.0, 2 M NaCl.

Reverse-Phase HPLC

Reverse-phase HPLC (RP-HPLC) was performed using a 4.6 mm×25 cm Vydac column (Separations Group) containing 5 µM packing with 330 angstrom pore size. The mobile phases were: "A", 0.05% trifluoroacetic acid (TFA) in water and "B", 0.05% TFA in acetonitrile. After loading the sample, the column was washed with "A" until the absorbance again reached baseline, and then eluted with the following linear gradients: 0% to 20% "B" over 20 minutes, 20% to 40% "B" over the next 80 minutes, and then 40% to 100% "B" over the next 20 minutes. All flow rates were 1 ml/min. Fractions were collected in siliconized glass tubes.

N-Terminal Amino Acid Sequence Analysis

Automated Edman degradation chemistry was used to determine N-terminal amino acid sequence. An Applied Biosystems, Inc., model 470A gas phase sequencer (Foster City, CA) was employed for the degradations [Hunkapiller, et al, *Methods Enzymol.* 91, 399-413 (1983)]. The respective PTH-amino acid derivatives were identified by RP-HPLC analysis in an on-line fashion employing an Applied Biosystems, Inc., Model 120A PTH Analyzer fitted with a Brownlee 2.1 mm I.D. PTH-$C_{18}$ column. Yields of PTH amino acids were determined by comparison with an external standard mixture. The average repetitive yield was calculated by linear regression analysis of the log pmolar yield versus cycle number plot.

Similarities between the obtained sequence and known sequences were investigated using the computer program FAST A [Pearson and Lipman, *Proc. Natl. Acad. Sci. USA* 85, 2444-2448 (1988)]. Similarity searches were also performed against the National Biomedical Research Foundation (NBRF) protein sequence data base [Sidney et al., *Nucleic Acids Res.* 16, 1869-1871 (1988), Release 17, Jun. 1988] and the translated GENBANK DNA base [Bilofsky and Burks, *Nucleic Acids Res.* 16, 1861-1864 (1988), Release 56, June 1988].

Tryptic peptides were prepared from reduced and alkylated hVPF. hVPF (1 nmole) was dissolved in 100 µl of 0.5 M Tris HCl, pH 8.5, 6 M guanidine-HCl, 1 mM EDTA, and 5 mM dithiothreitol. The solution was incubated for 30 minutes at 37° C. before the addition of sodium iodoacetate (to a final concentration of 5 mM) and incubation at 4° C overnight. After dialyzing against 2 M guanidine HCl, 0.01 M Tris-HCl, pH 8.5, and then 0.1 M ammonium bicarbonate, 1 µg of TPCK treated trypsin (Sigma Chemical Co., St. Louis, Mo.) was added and the solution incubated overnight at 37° C. Peptides were separated by RP-HPLC using a Nucleosil s, 5 micron, 100 Å, 4.6×250 mm column (Macherey-Nagel, Inc.). The flow rate was 1 ml/min at room temperature. A linear gradient of 0 to 90% acetonitrile in 0.1% trifluoroacetic acid run over 270 minutes was used for elution.

Electrophoresis

Sodium dodecyl sulfate-polyacrylamide gel electrophoresis (SDS-PAGE) was carried out on 10-15% gradient polyacrylamide gels using a Pharmacia Phast-System. The buffer systems and the silver staining protocol were those that were recommended by the manufacturer.

Antibodies and Immunoassays

Rabbit polyclonal antiserum to gVPF (designated F001) was prepared by immunizing a New Zealand White (NZW) rabbit with repeated injections of gVPF. The first injection was in Complete Freund's Adjuvant followed by boosts in Incomplete Freund's Adjuvant. gVPF was purified by preparative SDS-PAGE [Senger et al, *Science* 219 983-985 (1983)] following purification by the method of Senger et al. *Fed. Proc.* 46, 2102 (1987).

Sandwich enzyme linked immunosorbant assays (ELISA) for human and guinea pig VPF were performed as described below. The IgG fraction of F001 antiserum was purified using adsorption onto protein A-Sepharose. 500 ng/well of the IgG obtained from an 11th bleed serum was coated onto polystyrene microtiter plates for 3 hours. Then various known concentrations of human and guinea pig VPF were allowed to bind overnight. The concentrations were estimated from the maximal dilution which still produced a detectable response in the Miles permeability assay. This concentration was 50 ng/ml of VPF. The amount of bound antigen was detected with 500 ng/well biotin-a-gVPF IgG (11th bleed F001 antiserum) for 2 hours followed by 1/2000 dilution of horseradish peroxidase (HRP)-avidin (Cappel Labs) for 90 minutes. Wells were developed with the HRP substrate o-phenylenediamine-2HCl plus $H_2O_2$ and the absorbance was read at 490 nm in a BioTek reader.

It had been observed that the earlier bleeds of rabbit F001 contained a higher concentration and/or higher affinity of antibodies cross-reactive with hVPF compared to later bleeds. Therefore, an ELISA for hVPF was also performed with an early bleed (4th bleed) antiserum. It was performed under the same conditions as described above except that 1500 ng/well of a biotin-F001 IgG (4th bleed) was used to detect the amount of bound antigen.

Results

U-937 Permeability Enhancing Activity

The serum-free conditioned medium from U-937 cells in culture produced a positive response when tested in the Miles permeability assay. These results were unexpected since many cells do not produce a VPF-like activity as seen from Example 2, below. The Miles assay measures extravassation of Evan's blue dye-serum albumin complexes from the circulation after intradermal injection of a test material. However, the assay is non-specific and could measure positive response from a variety of substances, including, for example, histamine. It was therefore not known initially if the permeability enhancing activity produced by U-937 cells was related to guinea pig tumor VPF. To test this, the medium was mixed with an immunoadsorbent composed of protein A-Sepharose ® and IgG obtained from polyclonal antisera against gVPF. Most, but not all, of the permeability enhancing activity present in the U-937 medium was adsorbed using this procedure, but not when control IgG obtained from rabbits not immunized with gVPF was used instead. Most of the permeability enhancing activity secreted into the medium of U-937 cells therefore appeared to be related to guinea pig tumor derived VPF. However, as discussed below, even though hVPF shares some immunocrossreactivity with gVPF, it is immunologically distinct from gVPF.

hVPF Purification

Figure 1:
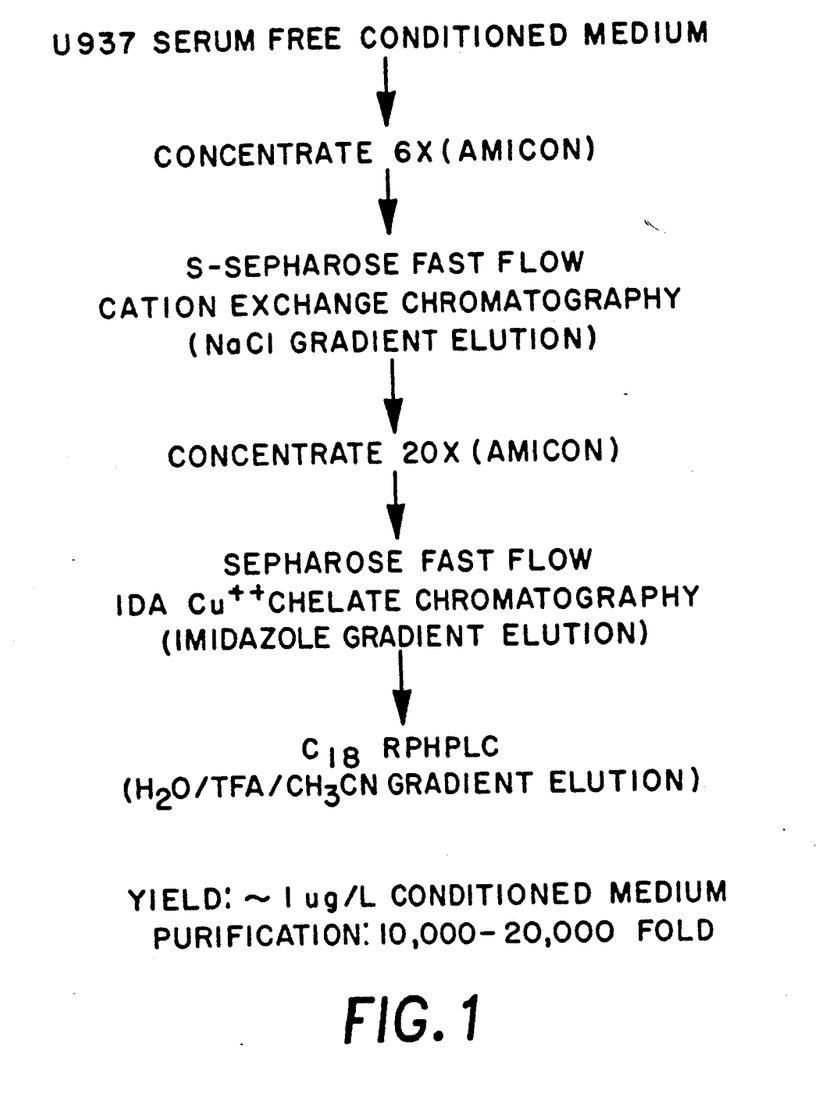
FIG. 1 is a schematic representation which shows the stepwise isolation of the human VPF (hVPF) from the conditioned cell culture medium of U-937 cells in one embodiment of the invention.
Figure 2A:
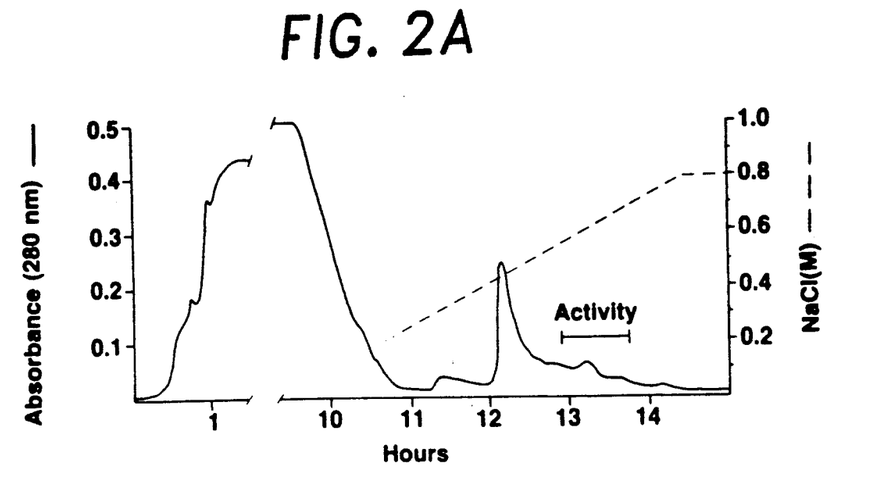
Figure 2B:
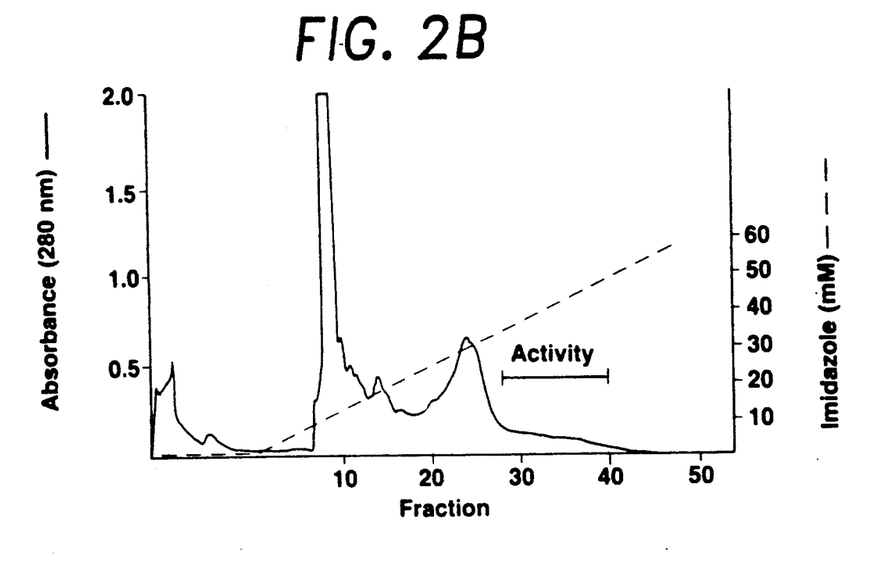
Figure 2C:
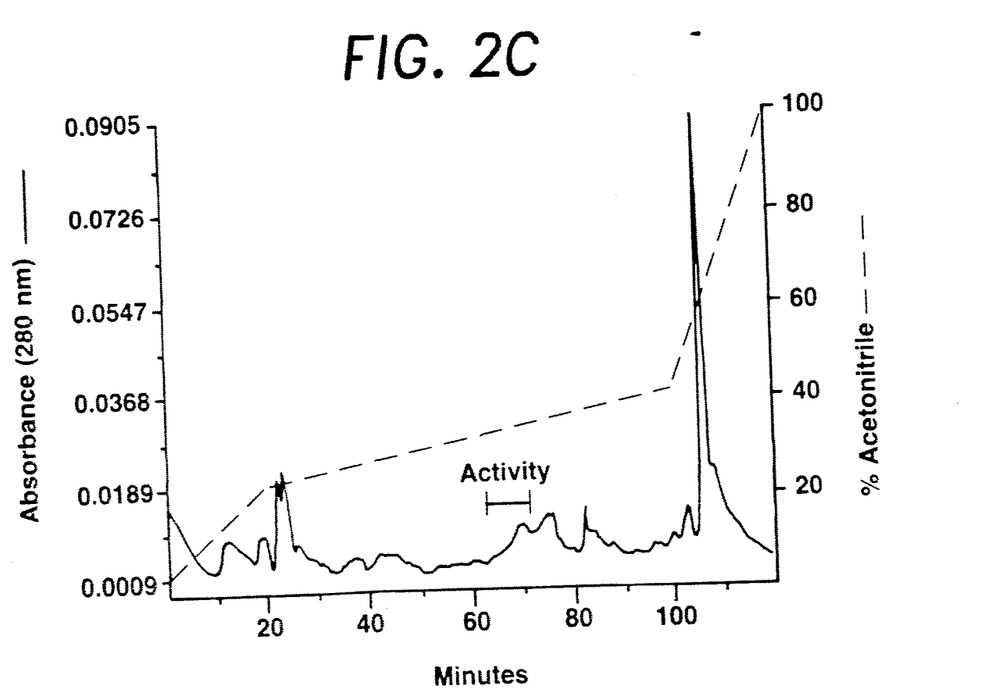
Figure 2D:
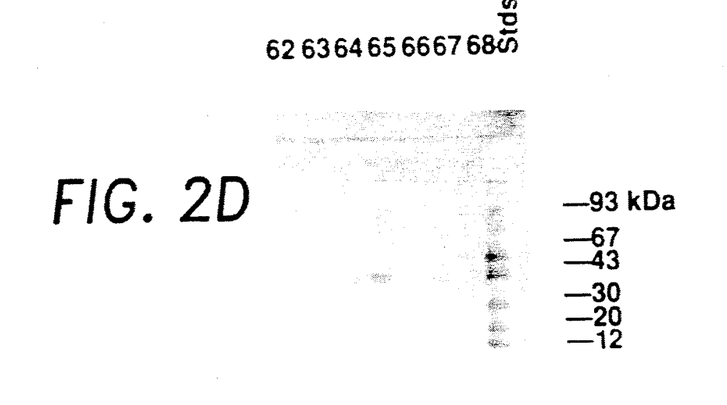

Initial attempts at purification of U-937 cell derived permeability enhancing activity employed the purification method previously used for gVPF as described by Senger et al, *Fed. Proc.* 46, 2102 (1987). The application of this method, or minor modifications thereof, did not produce homogeneous protein from U-937 cell conditioned medium, even though the chromatographic behaviour of the permeability enhancing activity was very similar to that of gVPF. A novel purification method was therefore developed that incorporated cation exchange chromatography, metal affinity chromatography, and RP-HPLC (FIG. 1). In the first step, concentrated conditioned medium was passed over an S Sepharose cation exchange column (FIG. 2A). About 50-70% of the permeability enhancing activity was bound to the column at pH 7.0. The non-adsorbed activity was not characterized. The bound activity was eluted with a gradient of sodium chloride, and after concentration by ultrafiltration, loaded onto a metal affinity column (FIG. 2B). All detectable activity was tightly bound by the copper/IDA/Sepharose column, and was eluted after most of the other proteins in a gradient of imidazole. The final step utilized RP-HPLC (FIG. 2C) and resulted in elution of a group of $M_r \sim 40$ kDa proteins in the fractions associated with the peak of permeability enhancing activity (FIG. 2D). This method has been repeated numerous times and it reproducibly yielded $M_r \sim 40$ kDa protein of about 90% or greater purity as analyzed by SDS-PAGE with silver staining or by N-terminal sequence analysis. Approximately 1-2 µg of pure protein can be obtained per liter of U-937 cell conditioned medium.

Dose Response of hVPF Induced Permeability Enhancement

Different amounts of hVPF were tested in the Miles permeability assay. The lowest dilution producing a positive response was at a hVPF concentration of about 2.75 nM. This corresponds to an injection dose of 22 ng, or 0.55 picomoles of $M_r$ 40 kDa hVPF. This is equivalent to only one-ninth the 200 ng required for a similar response by the gVPF described in U.S. Patent 4,456,550.

Amino Acid Sequence of hVPF hVPF was subjected to N-terminal amino acid sequence analysis (Table 1). Complete identity was observed between hVPF and the guinea pig tumor derived gVPF for the first 6 positions, but the sequence diverged for the next 4 amino acids sequenced. The identity is thus only 60% in this N-terminal region.

TABLE 1

Comparison of N-Terminal Sequences of hVPF and gVPF

| | Residue (pMole Yield) | |
|---|---|---|
| Cycle | hVPF | gVPF |
| 1 | Ala (627) | Ala (838) |
| 2 | Pro (427) | Pro (598) |
| 3 | Met (406) | Met (358) |
| 4 | Ala (130) | Ala (463) |
| 5 | Glu (85) | Glu (456) |
| 6 | Gly (55) | Gly (434) |
| 7 | Gly (76) | Glu (537) |
| 8 | Gly (150) | Gln (276) |
| 9 | Gln (34) | Lys (179) |
| 10 | Asn (29) | Pro (354) |

Approximately 1 nmole (about 40 μg as estimated by SDS-PAGE and silver staining) of hVPF was sequenced. The amino acids detected and the yield at each cycle (in parentheses) are shown. The average repetitive yield was 73%. These data are representative of several other runs on similar hVPF preparations.

In order to obtain internal sequence information, hVPF was reduced, carboxymethylated with iodoacetic acid, and treated with trypsin. The resulting peptides were then separated using RP-HPLC. Several of the isolated peptides were sequenced, as shown in Table 2. None of these sequences, nor the N-terminal sequences, showed significant homology to proteins present in published data bases. The novel hVPF of the present invention thus is substantially different from previously described proteins and from gVPF.

TABLE 2

Sequence of hVPF Tryptic Peptides

| Peptide | | | | | | | | | | | | | |
|---|---|---|---|---|---|---|---|---|---|---|---|---|---|
| 53 | Phe | Met | Asp | Val | Tyr | Gln | Arg | | | | | | |
| 71 | Ile | Phe | Lys | Pro | Ser | Cys | Val | Pro | Leu | Met | Arg | | |
| 93 | Val | Asp | Ile | Phe | Gln | Glu | Tyr | Pro | Asp | Glu | Ile | Glu | Tyr |
| | 1 | | | | 5 | | | | | 10 | | | |

Reduced and carboxymethylated hVPF was treated with trypsin and the peptides separated by RP-HPLC. Peptides that were well isolated were sequenced. The number designation corresponds to the fraction number in which the peptide appeared.

Reactivity of hVPF With Anti-gVPF Antibodies

Figure 3A:
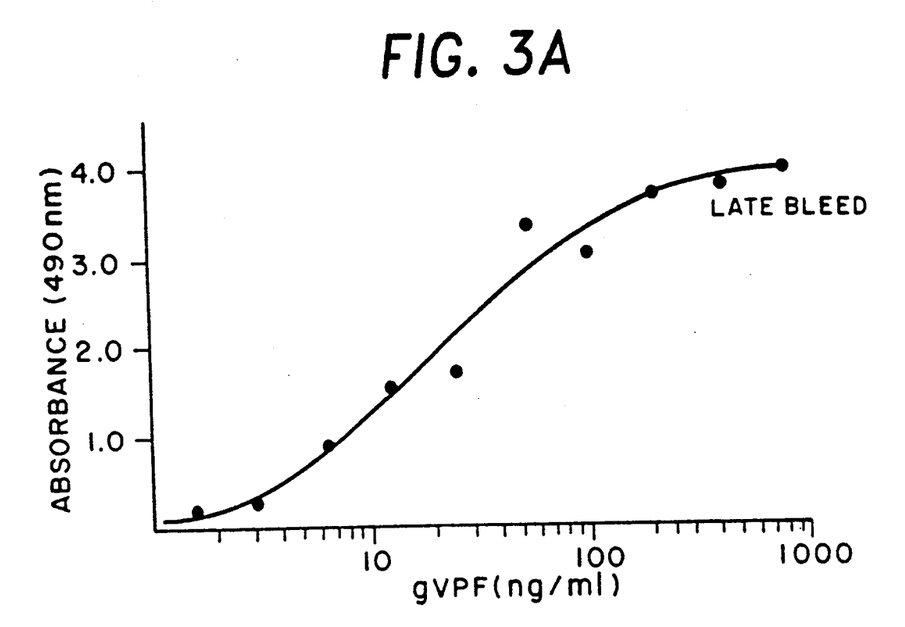
Figure 3B:
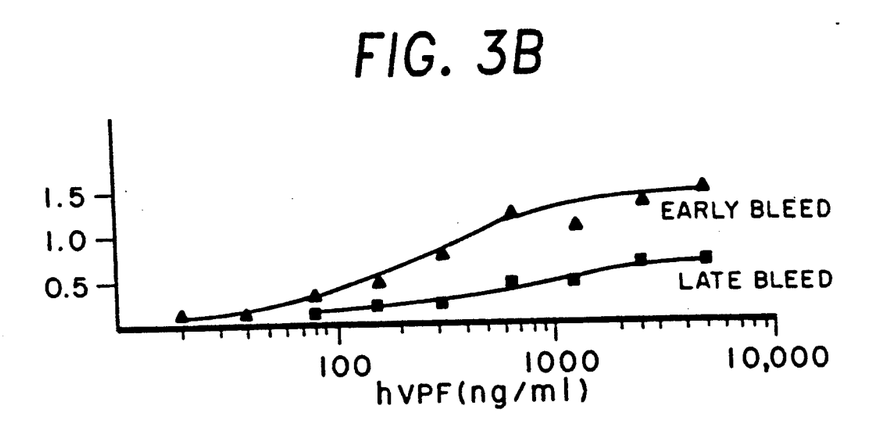

Polyclonal rabbit antibody against gVPF was tested for cross-reactivity with hVPF using a sandwich ELISA. FIG. 3 shows that hVPF is recognized by anti-gVPF IgG, but that the concentration of hVPF required for detection is about 10 fold higher than that for gVPF. Furthermore, although the maximum absorbance attained for hVPF (1.5 absorbance units above background) was significant, it was about 3 fold lower than that attained using gVPF as antigen. These results imply that the two proteins are related, but that hVPF is immunologically distinct from gVPF.

EXAMPLE 2 hVPF derived from U-937 cells was compared with VPF from several other cell lines by the Miles assay with the following results. The Mnng HOS human osteogenic sarcoma cell line was used as representative of the prior art human cell lines for production of VPF described by Senger et al., *Cancer Res.* 46, 5629–5632 (1986). The cells were extracted at a density of 1.5 to 2.0×10$^6$ cells/ml for 48 hours in serum-free basal medium, either RPMI 1640 or DME. The extract was collected, centrifuged to remove cells and debris, and then concentrated if necessary using Centricon 10 membranes (Amicon Corp.). The extracts were then tested in the Miles assay. The results as set forth in Table 3 demonstrate that the U-937 cells are outstandingly more effective as a producer of hVPF than the other human cell lines.

| Cell Line | Conditioned Media Concn. (a) | Miles Assay (units) (b) | Estimates of VPF Concn. (ng/ml) (c) |
|---|---|---|---|
| U-937(ATCC) Uncloned | 1X | 1 | 50 |
| U-937(ATCC) Cloned (d) | 1X | 2–8 | 100–400 |
| U-937(ATCC) Uncloned- Passaged through Nude mouse | 1X | 4–8 | 200–400 |
| Mnng HOS Human osteogenic sarcoma | 10X | +++ (e) | 30 (e) |
| JURKAT Human acute lymphoblastic leukemia | 12.3X | 1–2 | 4–8 |
| F2.11-2X Human T cell-T cell hybridoma | 10X | 0 | <5 |
| HFF Neonatal human foreskin fibroblasts | 26.6X | 0 | <2 |
| IMR 90 Human fetal lung fibroblasts | 26.6X | 5 | 10 |
| HEK Human embryonic kidney | 16.9X | 4 | 10 |
| 8387-M15 Human sarcoma | 36X | >16 | >20 |

(a) Conditioned media were concentrated X-fold as indicated prior to testing by the Miles assay.
(b) Activity of sample = greatest dilution of sample at which blue spot was detectable. 1 unit (u) = the amount of VPF in a sample producing the smallest detectable blue spot discernible from control injections without VPF.
(c) Estimate of VPF concentration in the unconcentrated spent media in ng/ml based on 1 unit activity = 50 ng/ml, a relationship established with the guinea pig Line 10 VPF of U.S. Pat. No. 4,456,550.
(d) Several clones, obtained by limiting dilution cloning procedures, produced activities in the 100–800 ng/ml range.
(e) This is an estimate based on the previously determined activity of Mnng HOS cells, since dilutions of the samples were not performed in this assay.

EXAMPLE 3

Materials

All reagents ad abbreviated designations, unless otherwise specified, are the same as described by Maniatis et al., *Molecular Cloning, A Laboratory Manual*, Cold Spring Harbor Laboratory, Cold Spring Harbor, N.Y., 1982. The λgt10 library was obtained from Clontech Laboratories, Inc., Palo Alto, Calif. (Cat. No. HL 1036a), which was prepared from U-937 cells treated with phorbol myristate acetate (PMA).

Methods

Oligonucleotide Screening of λgt10 Clontech library

Methods

Approximately $5 \times 10^5$ clones from a λgt10 cDNA library constructed from phorbol-ester stimulated U-937 cells (Clontech, Palo Alto, CA) were screened using two best-guess oligonucleotide probes. One probe, (5'-GTTCTGGCCGCCGCCCTCGGCCATAGGAGC-3'), which was based on N-terminal amino acid sequencing (amino acids 1-10 of hVPF) hybridized to a single gt10 clone. A second probe (5'-GTGGACATCTTCCAGGAGTACCCCGACGAGATCGAGTAC-3') based on sequence information from a tryptic peptide corresponding to amino acids 33-45 of hVPF hybridized to seven clones containing inserts ranging in size from 0.8 to 3.5 kb. The screening procedure was that of Ullrich et al., EMBO J. 3, 361-364 (1984), with the following modifications: purified yeast tRNA (Sigma Cat. No. R3001) (0.01mg/ml) was used instead of salmon sperm and the sodium pyrophosphate and ATP were deleted from the hybridization solution. The largest of these clones, clone 4, which was 3.5 kb in size, was subcloned into pUC9 (New England Biolabs), thereby generating plasmid vector pMON3044 (see FIG. 4) and 1195 bp of sequence was obtained using the general dideoxy-termination method of Sanger et al., Proc. Natl. Acad. Sci. USA 74, 5463-5467 (1977), employing reagents obtained from United States Biochemicals. The sequence corresponding to nucleotides 288 to 1110 was obtained by sequencing both strands of DNA. Nucleotides 147-288 were determined from only one strand, but were sequenced twice using two different sequencing primers.

DNA band migration patterns on agarose gels as a result of multiple restriction endonuclease digestion patterns of the pMON3044 construct indicated the orientation of the clone as shown in FIG. 4.

Results

A 3.5 Kb cDNA clone (designated VPF-4) was isolated from a λgt10 library prepared from mRNA isolated from phorbol-ester stimulated U-937 cells. This clone was transferred to the plasmid vector pUC9 to thereby form construct pMON3044. Then 1195 bp of sequence for the hVPF cDNA was generated. A variety of restriction endonucleases were used to determine the orientation of the cDNA for hVPF in the plasmid vector. Subjecting the cDNA to the selected endonuclease treatment demonstrated that approximately 1300 and 1600 bp of untranslated nucleotide sequences for the amino and carboxy termini, respectively, exist in the hVPF cDNA. The size of the hVPF/pUC9 construct (see FIG. 4) is approximately 6200 bp. This is the sum of approximately 3500 bp from the hVPF cDNA and approximately 2700 bp from the plasmid pUC9.

The predicted cDNA sequence demonstrated 100% homology with the N-terminus and several tryptic peptides previously determined using direct amino acid sequencing. These sequences correspond to amino acids 1-18, 17-23, 33-45 and 46-55, respectively. A signal sequence (amino acids -26 to -1) and a single N-linked glycosylation site at Asn 75 were also found. These results confirm that hVPF is a secreted and glycosylated protein.

A further comparison between the amino acid sequences of hVPF and gVPF was made by comparing the N-terminal sequence of the U-937 cell-derived hVPF as shown above and the sequence of gVPF determined by amino acid sequencing of purified gVPF from guinea pig Line 10 tumor cells as follows:

| | | | | | 5 | | | | 10 | | | | 15 |
|---|---|---|---|---|---|---|---|---|---|---|---|---|---|
| hVPF | Ala | Pro | Met | Ala | Glu | Gly | Gly | Gly | Gln | Asn | His | His | Glu | Val | Val |
| | * | * | * | * | * | * | | | * | | | * | * | * |
| gVPF | Ala | Pro | Met | Ala | Glu(5) | Gly | Glu | — | Gln | Lys(9) | Pro | Arg | Glu | Val | Val(14) |

| | | | | | 20 | | | | | 25 | | | | 30 |
|---|---|---|---|---|---|---|---|---|---|---|---|---|---|---|
| hVPF | Lys | Phe | Met | Asp | Val | Tyr | Gln | Arg | Ser | Tyr | Cys | His | Pro | Ile | Glu |
| | * | * | * | * | * | * | | * | * | * | * | | * | * | * |
| gVPF | Lys | Phe | Met | Asp | Val(19) | Tyr | Lys | Arg | Ser | Tyr(24) | Cys | Arg | Pro | Ile | Glu(29) |

| | | | | 35 | | |
|---|---|---|---|---|---|---|
| hVPF | Thr | Leu | Val | Asp | Ile | Phe | Gln |
| | * | * | * | * | * | * | * |
| gVPF | Met | Leu | Val | Asp | Ile(34) | Phe | Gln |

Comparison of the amino termini of VPF from guinea pig and human tumor cell lines demonstrate distinct differences. A gap between amino acid positions 7 and 8 in the gVPF sequence must be inserted for overlap to occur between the two proteins. Additionally, using numbering from hVPF, several areas of nonidentical residues are noted, namely at amino acids 7, 8, 10, 11, 12, 22, 27 and 31.

EXAMPLE 4

Expression of Permeability-Enhancing Activity by C-127 Cells Transfected with the hVPF Gene Serum-free conditioned medium was collected from three selected hVPF cell lines (VPF-25B, -29B, and -30B) transfected with a BPV expression vector containing the hVPF cDNA sequence, or from a control line (BPV-1123) transfected with the BPV vector only. This BPV vector contains the entire bovine papilloma virus genome ligated to the well-known pBR322 derivative of pML2. Medium was concentrated 5-fold using a Centricon-10 ultrafiltration device before performing the Miles permeability assay. A positive response was indicated by the appearance of a blue spot at the site of intradermal injection of sample into the guinea pig, indicating extravasation of Evan's blue dye from the circulation.

The hVPF cDNA was thus expressed in mammalian cells with a bovine papilloma virus (BPV) vector. This vector is based on the 100% viral genome and utilizes the mouse metallothionein I promoter and the SV40 Late poly A addition site to regulate the expression of foreign genes. The vector was linearized at the unique BamHI site between the promoter and poly A addition site. The 5' overhanding ends of the vector fragment were filled in with Klenow enzyme and dNTP's. Similarly, the plasmid containing the hVPF cDNA was digested with XmaI and the 1021 bp VPF fragment was isolated by gel electrophoresis. This blunt end fragment was then inserted into the vector by ligation. Mouse C-127 cells were cotransfected with the hVPF expression vector and pSV2neo by the calcium phosphate precipitation method as described by Howley et al., *Meth. Enzymol.* 101, 387–403 (1983). G418 (genticin) resistant transfectants were selected. Colonies were picked and expanded into stable lines for assay by the Miles assay.

Various other examples will be apparent to the person skilled in the art after reading the present disclosure without departing from the spirit and scope of the invention. It is intended that all such examples be included within the scope of the appended claims.

What is claimed is:

1. A DNA molecule encoding human vascular permeability factor comprising the nucleotide sequence:

```
1    GCGCAGACAG TGCTCCAGCG
              CGCGCGCTCC CCAGCCCTGC CCGGCCTCGG

51   GCCGGGAGGA AGAGTAGCTC
              GCCGAGGCGC CGAGGAGAGC GGGCCGCCCC

101  ACAGCCCGAG CCGGAGAGGG
              ACGCGAGCCG CGCGCCCCGG TCGGGCCTCC

151  GAAACC ATG AAC TTT CTG
              CTG TCT TGG GTG CAT TGG AGC CTT

193  GCC TTG CTG CTC TAC CTC
              CAC CAT GCC AAG TGG TCC CAG GCT

235  GCA CCC ATG GCA GAA GGA GGA
              GGG CAG AAT CAT CAC GAA GTG

277  GTG AAG TTC ATG GAT GTC TAT
              CAG CGC AGC TAC TGC CAT CCA

319  ATC GAG ACC CTG GTG GAC ATC
              TTC CAG GAG TAC CCT GAT GAG

361  ATC GAG TAC ATC TTC AAG CCA
              TCC TGT GTG CCC CTG ATG CGA

403  TGC GGG GGC TGC TGC AAT GAC
              GAG GGC CTG GAG TGT GTG CCC

445  ACT GAG GAG TCC AAC ATC ACC
              ATG CAG ATT ATG CGG ATC AAA

487  CCT CAC CAA GGC CAG CAC ATA
              GGA GAG ATG AGC TTC CTA CAG

529  CAC AAC AAA TGT GAA TGC AGA
              CCA AAG AAA GAT AGA GCA AGA

571  CAA GAA AAA AAA TCA GTT CGA
              GGA AAG GGA AAG GGG CAA AAA

613  CGA AAG CGC AAG AAA TCC CGG
              TAT AAG TCC TGG AGC GTT CCC

655  TGT GGG CCT TGC TCA GAG CGG
              AGA AAG CAT TTG TTT GTA CAA

697  GAT CCG CAG ACG TGT AAA TGT
              TCC TGC AAA AAC ACA GAC TCG

739  CGT TGC AAG GCG AGG CAG CTT
              GAG TTA AAC GAA CGT ACT TGC

781  AGA TGT GAC AAG CCG AGG CGG
              TGA GCCGGGCAGG AGGAAGGAGC

825  CTCCCTCAGG GTTTCGGGAA
              CCAGATCTCT CACCAGGAAA GACTGATACA

875  GAACGATCGA TACAGAAACC
              ACGCTGCCGC CACCACACCA TCACCATCGA

925  CAGAACAGTC CTTAATCCAG
              AAACCTGAAA TGAAGGAAGA GGAGACTCTG

975  CGCAGAGCAC TTTGGGTCCG
              GAGGGCGAGA CTCCGGCGGA AGCATTCCCG

1025 GGCGGGTGAC CCAGCACGGT
              CCCTCTTGGA ATTGGATTCG CCATTTTATT

1075 TTTCTTGCTG CTAAATCACC
              GAGCCCGGAA GATTAGAGAG TTTTATTTCT

1125 GGGATTCCTG TAGACACACC
              CACCCACATA CATACATTTA TATATATATA

1175 TATTATATAT ATATAAATTA A.
```

2. A cDNA molecule which encodes human vascular permeability factor comprising the amino acid sequence:

Ala Pro Met Ala Glu Gly Gly Gly Gln Asn His His Glu Val Val Lys Phe Met Asp Val Tyr Gln Arg Ser Tyr Cys His Pro Ile Glu Thr Leu Val Asp Ile Phe Gln Glu Tyr Pro Asp Glu Ile Glu Tyr Ile Phe Lys Pro Ser Cys Val Pro Leu Met Arg Cys Gly Gly Cys Cys Asn Asp Glu Gly Leu Glu Cys Val Pro Thr Glu Glu Ser Asn Ile Thr Met Gln Ile Met Arg Ile Lys Pro His Gln Gly Gln His Ile Gly Glu Met Ser Phe Leu Gln His Asn Lys Cys Glu Cys Arg Pro Lys Lys Asp Arg Ala Arg Gln Glu Lys Lys Ser Val Arg Gly Lys Gly Lys Gly Gln Lys Arg Lys Arg Lys Lys Ser Arg Tyr Lys Ser Trp Ser Val Pro Cys Gly Pro Cys Ser Glu Arg Arg Lys His Leu Phe Val Gln Asp Pro Gln Thr Cys Lys Cys Ser Cys Lys Asn Thr Asp Ser Arg Cys Lys Ala Arg Gln Leu Glu Leu Asn Glu Arg Thr Cys Arg Cys Asp Lys Pro Arg Arg.

3. A vector comprising the cDNA molecule of claim 1.

4. A vector comprising the cDNA molecule of claim 2.

5. A mammalian host cell transfected with the vector of claim 3.

6. A mammalian host cell transfected with the vector of claim 4.

7. The mammalian host cell of claim 5 wherein the mammalian host cell is a mouse C-127 cell.

8. The mammalian host cell of claim 6 wherein the mammalian host cell is a mouse C-127 cell.

* * * * *